United States Patent
Case-Gustafson et al.

(10) Patent No.: US 9,681,994 B2
(45) Date of Patent: Jun. 20, 2017

(54) ELECTRICALLY CONDUCTIVE SKIN COVERING ELEMENTS

(71) Applicants: Pamela S. Case-Gustafson, Chapel Hill, NC (US); Vincent K. Gustafson, Chapel Hill, NC (US)

(72) Inventors: Pamela S. Case-Gustafson, Chapel Hill, NC (US); Vincent K. Gustafson, Chapel Hill, NC (US)

(*) Notice: Subject to any disclaimer, the term of this patent is extended or adjusted under 35 U.S.C. 154(b) by 58 days.

(21) Appl. No.: 14/550,733

(22) Filed: Nov. 21, 2014

(65) Prior Publication Data

US 2015/0182384 A1 Jul. 2, 2015

Related U.S. Application Data

(63) Continuation of application No. PCT/US2013/041966, filed on May 21, 2013.
(Continued)

(51) Int. Cl.
*G06F 3/044* (2006.01)
*A61F 13/15* (2006.01)
(Continued)

(52) U.S. Cl.
CPC .... *A61F 13/15203* (2013.01); *A61F 13/0203* (2013.01); *G06F 3/044* (2013.01);
(Continued)

(58) Field of Classification Search
CPC . A61F 13/15203; A61F 13/0203; G06F 3/044
See application file for complete search history.

(56) References Cited

U.S. PATENT DOCUMENTS

| 4,539,996 A | 9/1985 | Engel |
| 4,549,653 A | 10/1985 | Lauritzen |

(Continued)

FOREIGN PATENT DOCUMENTS

| CN | 101407631 A | 4/2009 |
| CN | 201469257 U | 5/2010 |

(Continued)

OTHER PUBLICATIONS

International Search Report (Form PCT/ISA/210) for International Patent Application No. PCT/US2013/041966 mailed on Nov. 21, 2013, 2 pages.

(Continued)

*Primary Examiner* — Ariel Balaoing
(74) *Attorney, Agent, or Firm* — Vincent K. Gustafson (57) ABSTRACT

Skin covering elements utilize conductive regions including electrically conductive materials may be arranged to enable a user to actuate a capacitive touchscreen such as through a centrally arranged absorptive pad and/or laterally through a carrier. Embodiments directed to adhesive bandages and athletic tapes are provided. A method includes applying an adhesive bandage to a user and depressing a portion of the bandage against a surface of a capacitive touchscreen to control or operate a function of an electronic device. Conductive regions may be also arranged to communicate with an electrical interface, such as for resistive heating of skin of a user and/or providing communication with one or more sensors.

20 Claims, 4 Drawing Sheets

Related U.S. Application Data (60) Provisional application No. 61/651,000, filed on May 24, 2012.

(51) Int. Cl.
*A61F 13/02* (2006.01)
*A61B 5/11* (2006.01)
*A61B 5/00* (2006.01)

(52) U.S. Cl.
CPC ............... *A61B 5/11* (2013.01); *A61B 5/6831* (2013.01); *A61F 2013/15284* (2013.01)

(56) References Cited

U.S. PATENT DOCUMENTS

| | | | |
|---|---|---|---|
| 4,750,482 A * | 6/1988 | Sieverding | A61L 15/58 522/129 |
| 4,926,851 A | 5/1990 | Bulley | |
| 5,024,227 A | 6/1991 | Schmid | |
| 6,004,253 A | 12/1999 | Riedel et al. | |
| 6,232,366 B1 | 5/2001 | Wang et al. | |
| 6,362,388 B1 | 3/2002 | Lucas | |
| 7,863,495 B2 | 1/2011 | Aali | |
| 7,999,023 B2 | 8/2011 | Menon et al. | |
| 8,067,662 B2 | 11/2011 | Aali et al. | |
| 2002/0082668 A1 * | 6/2002 | Ingman | A61N 1/20 607/98 |
| 2003/0149349 A1 | 8/2003 | Jensen | |
| 2011/0310064 A1 * | 12/2011 | Keski-Jaskari | G06F 3/044 345/178 |
| 2012/0019464 A1 | 1/2012 | DiDato | |
| 2013/0030341 A1 | 1/2013 | Freer et al. | |
| 2013/0178812 A1 | 7/2013 | Flach | |
| 2013/0268094 A1 * | 10/2013 | Van Wiemeersch | A61F 2/54 623/57 |
| 2015/0242001 A1 * | 8/2015 | Stojanovski | G06F 3/03545 602/42 |

FOREIGN PATENT DOCUMENTS

| | | |
|---|---|---|
| DE | 10306187 A1 | 9/2004 |
| KR | 20120069025 A | 6/2012 |
| WO | 03-090654 A1 | 11/2003 |
| WO | 2005-060889 A1 | 7/2005 |
| WO | 2008-071941 A2 | 6/2008 |
| WO | 2013-019266 A1 | 2/2013 |

OTHER PUBLICATIONS

Lin, Chin-Teng, et al., "Novel Dry Polymer Foam Electrodes for Long-Term EEG Measurement", IEEE Transactions on Biomedical Engineering, vol. 58, No. 5, pp. 1200-1207, May 2011.
American White Cross First Aid Brand Adhesive Bandages Catalog, 2013, Derma Sciences, Inc., Princeton, NJ, 33 pages.

* cited by examiner

ELECTRICALLY CONDUCTIVE SKIN COVERING ELEMENTS

STATEMENT OF RELATED APPLICATION

This application is a continuation under 35 U.S.C. §120 of International Patent Application No. PCT/US2013/041966 filed on May 21, 2013, which claims priority of U.S. Provisional Patent Application No. 61/651,000 filed on May 24, 2012. The entire contents of the foregoing applications are hereby incorporated by reference herein.

TECHNICAL FIELD

Subject matter herein relates to skin covering elements including, but not limited to, adhesive bandages, athletic tapes, and the like.

BACKGROUND

A touchscreen is an electronic visual display that can detect the presence and location of a touch within the display area. The term generally refers to touching the display of the device with a finger or hand. Touchscreens are common in devices such as smartphones, video game consoles, personal digital assistants, satellite navigation devices, computer monitors, and other information appliances. A touchscreen enables a user to interact directly with what is displayed, rather than indirectly with a pointer controlled by a mouse or touchpad.

Although certain touchscreens can be operated with a stylus instead of a user's finger or hand, many users prefer to operate a touchscreen directly with a finger or hand to avoid the need for carrying a stylus (which is subject to loss or breakage), and to avoid awkward motion or discomfort associated with operating an information appliance using a touchscreen.

Different touchscreen technologies embodying different methods of sensing touch are known, including resistive, surface acoustic wave, and capacitive technologies. A resistive touchscreen panel includes multiple layers, including two thin, transparent electrically-resistive layers that are separated by a thin gap. When an object (e.g., a fingertip or stylus tip) presses down on an outer surface of a resistive touchscreen panel, the transparent electrically-resistive layers contact one another locally, and a signal is detected based on position of the contact. Unfortunately, resistive touchscreens suffer from relatively poor contrast due to additional reflections from the extra layer of material placed over the screen, and such touchscreens may be cumbersome to use.

Surface acoustic wave (SAW) touchscreens use ultrasonic waves that pass over the touchscreen panel. When the panel is touched, a portion of the wave is absorbed, and the resulting change in ultrasonic waves registers the position of the touch event. Unfortunately, surface wave touchscreen panels may be easily damaged by outside elements, and surface contaminants can interfere with their operation.

A capacitive touchscreen panel consists of an insulator such as glass, coated with a transparent conductor such as indium tin oxide. As the human body is also an electrical conductor, touching the surface of the screen results in a distortion of the screen's electrostatic field, which is measurable as a change in capacitance. Such location is determined and sent to a controller for processing. One characteristic of capacitive touchscreens is that they require direct contact with an electrical conductor for operation. In cold weather, usability of devices including capacitive touchscreens may be impaired by conventional gloves which are insulating in character, although special-application gloves with a patch of electrically conductive material arranged at the fingertip for intermediate contact between a user's finger and a capacitive touchscreen have been developed.

Although special-application gloves with conductive fingertips are useful to expand the utility of capacitive touch screens, it would be desirable to expand the utility of touch screens in other contexts where a user's skin may be covered by an insulating material such an adhesive carrier and/or wound covering, or where a user lacks conductive tissue at one or more regions (e.g., over a prosthetic limb).

Figure 1A:
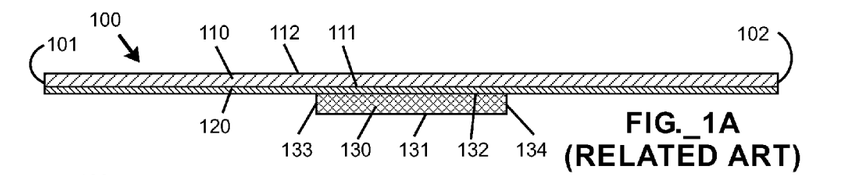
FIG. 1A is a side cross-sectional schematic view of a first conventional adhesive bandage including a carrier, an adhesive layer, and an absorptive pad affixed to the adhesive layer.
Figure 1B:
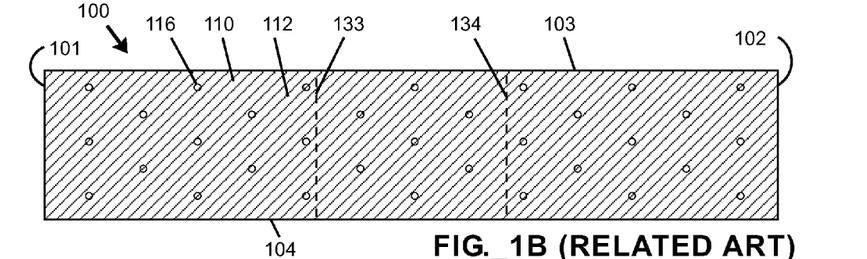
FIG. 1B is a top plan view of the conventional adhesive bandage of FIG. 1A.
Figure 1C:
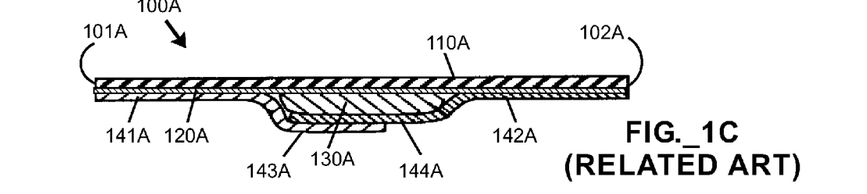
FIG. 1C is a side cross-sectional schematic view of a second conventional adhesive bandage consistent with the bandage according to FIGS. 1A-1B, with two sections of a release layer arranged in partially overlapping relationship over an adhesive pad.

Adhesive bandages including a central pad area and adjacent adhesive areas are well known in the art and are popular as first aid wound dressings. Such bandages may be commercially produced using roll-based machines called converters. With reference to FIGS. 1A-1B, a conventional adhesive bandage 100 generally includes an elongated strip of polymeric or fabric backing or carrier material 110 having two ends 101, 102, having an outer surface 112, and having an inner surface 111 coated with a pressure sensitive adhesive (PSA) 120. A gauze or sponge absorbent pad 130 is secured along an outer surface 132 to a surface of the PSA 120 in a central location to serve as the wound covering material. An inner wound facing surface 131 of the pad 130 may be plastic coated or otherwise treated to prevent the pad 130 from adhering to a wound. The pad 130 includes lateral boundaries 133, 134. Pores or holes 116 may be formed in the carrier 110 for ventilation. Referring to FIG. 1C, a conventional adhesive bandage 100A (with carrier 110A, adhesive layer 120A, absorbent pad 130A, and ends 101A-101B) may include plastic coated release strips 141A, 142 placed over adhesive layer 120A with non-adhered portions 143A, 144A overlapping the absorbent pad 130A. The entire assembly may be enclosed in a sealed package (not shown) and sterilized to be ready for use. In conventional adhesive bandages, at least the absorbent pad, and in some instances also the backing material, is not sufficiently conductive to permit a user to actuate a capacitive touchscreen when the absorbent pad is placed between a user's skin and the touchscreen.

Adhesive bandages with metal-containing portions are known, but do not address the problem of permitting a user to control a capacitive touchscreen. EasyAG (a/k/a Silver-Lon) antimicrobial silver adhesive strips (commercially available from Argentum Medical, LLC, Chicago, Ill., USA (www.silverlon.com)) include an absorbent pad with silver material arranged on the inner surface thereof for contact with a wound. Although the silver material provides low electrical resistance in a lateral direction (i.e., approximately 5 Ohms from lateral end to lateral end, as measured with a digital multimeter), a distal surface of the absorbent pad appears to lack silver material (as visible by a white appearance) and is covered by a polymeric carrier. Various tests performed of the EasyAG (a/k/a SilverLon) antimicrobial silver adhesive strips in conjunction with an Apple iPhone® 4s confirmed that when the bandage was placed over a user's fingertip with the absorbent pad arranged between the user's finger and the capacitive screen of the phone, the absorbent pad portion prevented the user from controlling the phone.

Various commercially adhesive bandages (and aluminum foil) were tested to determine their efficacy in passing a signal from a user's finger to the capacitive touchscreen of an Apple iPhone® 4s. Results are summarized in the following Table 1.

TABLE 1

Summary of Results of Testing of Conventional Bandages and Foil

|  | Band-Aid ® Flexible Fabric | Band-Aid ® Sport Strip ® | Band-Aid ® Sheer Comfort-+Flex ™ | EasyAG (a/k/a SilverLon) antimicrobial silver adhesive strips | Aluminum (metal) foil |
|---|---|---|---|---|---|
| Direct signal conduction, carrier + adhesive | No | YES (single layer or doubled) | YES (single layer or doubled) | YES (single layer or doubled) | n/a |
| Direct signal conduction, carrier + adhesive + absorbent pad | No | No | No | No | n/a |
| Lateral signal conduction (1 cm), carrier + adhesive | No | No | No | No | n/a |
| Direct signal conduction, adhesive + carrier + aluminum foil overlaid over carrier | No | No | No | No | n/a |
| Lateral signal conduction (1 cm), adhesive + carrier + aluminum foil overlaid over carrier | No | No | No | No | n/a |
| Direct signal conduction, aluminum foil only | n/a | n/a | n/a | n/a | YES |
| Lateral signal conduction (1 cm), aluminum foil only | n/a | n/a | n/a | n/a | YES |

As indicated in Table 1, certain bandages permitted a touchscreen to be controlled through carrier and adhesive portions intermediately arranged between the user's skin and the touchscreen; however, none of the tested adhesive bandages enabled a user to control a capacitive touchscreen (i) through an absorbent pad intermediately arranged between the user's skin and the touchscreen, or (ii) through a carrier and adhesive when a point of contact of the user's skin was separated about 1 centimeter laterally apart from a point of contact with the touchscreen (i.e., by attempting to actuate the touchscreen using an eraser end of a pencil, with adhesive and carrier intermediate arranged between the eraser end and the touchscreen, with the eraser end being separated about 1 centimeter apart from a portion of the adhesive and carrier adhered to the user's skin). Overlaying carrier portions of such bandages with aluminum foil did not enhance conduction sufficiently to permit a capacitive touchscreen to be controlled. In comparison, aluminum foil alone intermediately arranged between a user's skin and a capacitive touchscreen permitted the touchscreen to be controlled—whether directly or laterally separated by 1 cm.

Thermally conductive wound coverings have been developed recently. For example, U.S. Patent Application Publication No. 2013/0030341 A1 to Freer et al. published on Jan. 31, 2013 discloses medical wound covering apparatuses that are effective for treatment of tissue burns. An extremely thin layer of thermally conductive metal such as aluminum is arranged at the base of a substrate and adapted to be in direct contact with a burn wound, with an outer surface of the substrate having a heat-dissipation-enhancing topography (e.g., raised surface features) to help cool burns faster by enhancing thermal convection properties. Embodiments illustrated at FIGS. 25-29 of such U.S. publication to Freer et al. discloses use of an intermediate layer 12 including absorbent material forming a window adjacent to a peripheral border of the wound covering, and with such material being intermediately arranged between the thermally conductive metal layer and a self-adhesive carrier layer that also forming a window adjacent to a peripheral border of the wound covering. Such publication to Freer et al. discloses that the centrally arranged conductive metal layer is to be arranged to directly contact the wound of a user to provide the critical function of dissipating heat from a burn wound, without any absorbent pad arranged along a central portion of the wound covering apparatus (which would otherwise interfere with the heat dissipation function).

With respect to control of a capacitive touchscreen, similar difficulties arise when portions of a user's skin are covered with self-adhesive athletic tape (e.g., including cotton carrier material), which is insufficiently conductive to permit a user to actuate a capacitive touchscreen.

Self-adhesive athletic tape typically includes a cotton carrier with adhesive arranged on one side thereof. Such tape is commonly used to wrap joint areas (e.g., ankles, wrists, fingers, etc.) to provide added support and stability, and/or to reduce swelling (e.g., following joint injury). In certain instances, joints wrapped with athletic tape may be stiff and resist movement, particularly in cold ambient conditions.

It would be desirable to provide skin covering elements enabling a user to actuate a capacitive touchscreen through skin covering elements of various types, including skin covering elements comprising adhesives. It would also be desirable to reduce stiffness of joints or tissues wrapped with athletic tape. It would further be desirable to enable a skin covering element to communicate with at least one electrical device. Various embodiments as disclosed herein address one or more of the foregoing concerns.

SUMMARY

Various aspects of the present invention relate to skin covering elements (including but not limited to adhesive bandages and athletic tapes) utilizing conductive regions including electrically conductive materials. In certain embodiments, conductive regions are arranged to enable a user to actuate a capacitive touchscreen, such as through an absorptive pad and/or laterally through a carrier. In certain embodiments, conductive regions are arranged in conductive electrical communication with at least one electrical interface, such as may be useful to permit resistive heating of a skin covering element and/or provide communication with one or more sensors.

In one aspect, the invention relates to an adhesive bandage adapted to adhere to skin of a user for covering a wound, the adhesive bandage comprising: a carrier including an inner face, an outer face, and a pressure-sensitive adhesive arranged along the inner face; and an absorbent pad arranged along at least a central portion of the inner face and arranged to contact a wound of a user; wherein the adhesive bandage comprises at least one of the following features (a) and (b): (a) an electrically conductive material is arranged in or on the absorbent pad to provide an electrically conductive path extending between a first face of the absorbent pad to a second face of the absorbent pad; and (b) an electrically conductive material is arranged in or on the carrier to provide an electrically conductive path extending between (i) skin of the user not covered by the absorbent pad and (ii) a portion of the carrier covering the absorbent pad. Another aspect of the invention relates to a method utilizing the foregoing adhesive bandage, comprising applying the adhesive bandage to at least one of skin and fingernail of a user, and depressing a portion of the adhesive bandage against a surface of a capacitive touchscreen of an electronic device to control or operate at least one function of the electronic device.

Another aspect of the invention relates to an athletic tape comprising: a fabric-based carrier including an inner face, an outer face, and an electrically conductive material extending between the inner face and the outer face; and an electrically conductive pressure-sensitive adhesive arranged along the inner face of the carrier. A further aspect of the invention relates to a method utilizing the foregoing athletic tape, comprising applying the athletic tape to skin of a user, and depressing a portion of the athletic tape against a surface of a capacitive touchscreen of an electronic device to control or operate at least one function of the electronic device.

Another aspect of the invention relates to a skin covering element comprising a carrier including an inner face, an outer face, and a first and a second electrically conductive region extending lengthwise along the carrier; a pressure-sensitive adhesive arranged along the inner face of the carrier; and a first electrical interface in conductive electrical communication with the first and the second electrically conductive region, wherein the first electrical interface is arranged to permit electrical communication with an electrical device. A further aspect of the invention relates to a method utilizing the foregoing skin covering element, comprising applying the skin covering element to skin of a user; connecting an electrical device to the skin covering element via the first electrical interface; and transmitting or receiving at least one electrical signal using the electrical device, the first electrically conductive region, and the second electrically conductive region.

In another aspect, any of the foregoing aspects, and/or various separate aspects and features as described herein, may be combined for additional advantage.

Other aspects, features and embodiments of the invention will be more fully apparent from the ensuing disclosure and appended claims.

DETAILED DESCRIPTION

Various aspects of the present invention relate to skin covering elements (including but not limited to adhesive bandages) utilizing conductive materials that enable a user to actuate a capacitive touchscreen, or to cooperate with an electrical device to transmit and/or to receive at least one signal. In certain embodiments directed to skin covering elements such as (but not limited to) adhesive bandages, at least one electrically conductive path may be provided between a first face and a second face of an absorbent pad, and/or at least one electrically conductive path may be provided (e.g., laterally through a carrier) between (i) skin of a user not covered by the absorbent pad and (ii) a portion of the carrier covering the absorbent pad. In certain embodiments directed to skin covering elements such as (but not limited to) athletic tape, at least one electrically conductive path may be provided laterally through a carrier, and/or through faces of multiple carrier layers when arranged in overlapping relationship. In certain embodiments directed to skin covering elements, multiple electrically conductive regions extend lengthwise along a carrier that includes a pressure sensitive adhesive along an inner face thereof, with a first electrical interface in conductive electrical communication with the first and the second electrically conductive region, wherein the first electrical interface is arranged to permit electrical communication with an electrical device. Methods of fabricating and using such skin covering elements are further provided.

Unless otherwise defined, terms used herein should be construed to have the same meaning as commonly understood by one of ordinary skill in the art to which this invention belongs. It will be further understood that terms used herein should be interpreted as having a meaning that is consistent with their meaning in the context of this specification and the relevant art, and should not be interpreted in an idealized or overly formal sense unless expressly so defined herein.

Embodiments of the invention are described herein with reference to illustrations (e.g., cross-sectional views, plan views, and/or perspective views) that are schematic illustrations of idealized embodiments of the invention. Variations from the shapes of the illustrations as a result, for example, of manufacturing techniques and/or tolerances, are to be expected, such that embodiments of the invention should not be construed as limited to particular shapes illustrated herein. This invention may be embodied in different forms and should not be construed as limited to the specific embodiments set forth herein. In the drawings, the size and relative sizes of layers and regions may be exaggerated for clarity.

Unless the absence of one or more elements is specifically recited, the terms "comprising," "including," and "having" as used herein should be interpreted as open-ended terms that do not preclude the presence of one or more elements.

It will be understood that when an element such as a layer or region is referred to as being "on" another element, it can be directly on the other element or intervening elements may be present. Moreover, relative terms such as "outer", "inner," "over," and the like may be used herein to describe a relationship of one layer or region relative to another layer or region as illustrated in the figures. It will be understood that these terms are intended to encompass different orientations of a skin covering in addition to the orientation depicted in the figures.

Certain skin covering elements as described herein include at least one adhesive material (e.g., a pressure sensitive adhesive (PSA)) arranged to contact a user's skin. Examples of skin covering elements incorporating pressure sensitive adhesive material include adhesive bandages and athletic tape. If adhesive is provided in the form of an adhesive layer, then such an adhesive layer may be continuous or non-continuous in character according to various embodiments.

In certain embodiments, an adhesive used with a skin covering element includes an electrically conductive material. Various types of skin-compatible, electrically conductive adhesives are known. For example, U.S. Pat. No. 6,232,366 to Wang, et al. (which is hereby incorporated by reference herein) discloses a skin-compatible, hot-melt processible, pressure-sensitive adhesive. Such adhesive comprises, for example, (i) between about 30 to 45 parts by weight of a copolymer comprised of between about 30 to 45 parts by weight of a (meth)acrylate ester monomer having $C_4$-$C_{20}$ alkyl chains, and between about 55 to 70 parts by weight of an acidic comonomer; (ii) between about 0 to 35 parts by weight of a hydrophilic plasticizer; (iii) between about 20 to 40 parts by weight of water, (iv) between about 0 to 3 parts by weight of a water soluble salt, (v) between about 10 to 20 parts by weight of a surfactant, and (vi) between about 0.5 to 10 parts by weight of a polymer having amine functionality. U.S. Pat. No. 6,232,366 discloses eight specific formulations described in Examples 1 to 8 thereof, with samples of each Example according to such patent being laminated onto an Ag/AgCl polyester backing and cut into 2.5 cm×2.5 cm (1 inch×1 inch) squares, adhered back to back (i.e., adhesive to adhesive), and subjected to AC impedance testing at 10 Hz. AC impedance values for the eight Examples according to U.S. Pat. No. 6,232,366 were represented in Table 2 of such patent, with values (ranging from lowest to highest) of 30, 38, 50.5, 65, 143.5, 156, 201, and 227 Ohms.

Additional skin-compatible, electrically conductive adhesives are disclosed in U.S. Pat. No. 4,848,353 to Engel (which is hereby incorporated by reference herein). U.S. Pat. No. 4,848,353 discloses an electrically-conductive, pressure-sensitive adhesive having a polymeric matrix comprised of copolymers of hydrogen bond donating monomer (for example acrylic acid) and hydrogen bond accepting monomers (for example N-vinylpyrrolidone). The polymeric matrix is homogeneously mixed with an electrically-conductive plasticizing solution comprised of from 0% to 98% by weight water-soluble, polar organic compound (for example glycerol), 2% to 100% by weight water, and 0 to 12% by weight water-soluble salt. The composition contains from about 12% to 50% by weight non-volatile copolymer matrix and the hydrogen bond donating sites on the copolymer matrix are from about 5% to about 95% neutralized. Free radical polymerization methods of making the composition are also disclosed. One specific implementation according to U.S. Pat. No. 4,848,353 provides a pressure-sensitive adhesive composition comprising: (i) a conformable, cohesive, adhesive copolymer matrix formed by free radical polymerizing an adhesive precursor comprising a carboxylic acid as a water-soluble hydrogen bond donating monomer, N-vinyl pyrrolidone as a water-soluble hydrogen bond accepting monomer, and a polymerization initiator, wherein the molar ratio of hydrogen bond accepting sites to hydrogen bond donating sites available on the monomers is from about 1:3 to about 6:1 and wherein the weight ratio of carboxylic acid to N-vinyl pyrrolidone is from about 1:2 to about 3:1; and (ii) a plasticizing, electrically-conductive solution comprised of from about 0 to 98% by weight water-soluble, polar organic compound, about 2 to 100% by weight water, and about 0 to 12% by weight water-soluble salt, wherein the composition is substantially homogeneous, contains from about 12% to about 50% by weight non-volatile copolymer matrix, and the hydrogen bond donating sites on the copolymer matrix are from about 5% to about 80% neutralized. U.S. Pat. No. 4,848,353 indicates that diagnostic biomechanical electrodes including polyester coated with tin and further coated with the above-described pressure-sensitive adhesive having a conductive adhesive surface area of 6.5 cm$^2$ (1 inch$^2$) and a conductive adhesive thickness of 0.9 mm (35 mil), when tested in pairs adhered together with such adhesive, exhibit an impedance in Ohms (at a 10 Hz frequency) not exceeding 2000 Ohms, more preferably not exceeding 1000 Ohms.

In certain embodiments, electrical conductive of adhesive layers may be enhanced by dissolution or dispersion of electrically conductive material (e.g., metals and/or electrically conductive polymers) in the adhesive.

In certain embodiments, an absorptive pad of an adhesive bandage includes electrically conductive material sufficient to provide an electrically conductive path extending between a first face and a second opposing face of the pad. Examples of electrically conductive material include, but are not limited to, metals and electrically conductive polymers. Although silver has been recognized as having anti-bacterial properties and may be used in certain embodiments, any suitably conductive metal (e.g., aluminum, chromium, copper, silver, gold, titanium, tin, tungsten, etc.) or metal alloy (e.g., brass, bronze, stainless steel, etc.) may be used in other embodiments. In certain embodiments, one or more electrically conductive materials may be arranged over non-conductive cores or substrates, such as (for example) metal coating arranged over cotton or synthetic thread. Electrically conductive material may be provided in the form of threads, strips, mesh, matrices, foil, and/or applied coating(s). In certain embodiments, electrically conductive material is stitched into or through, or woven into or through, an absorptive pad. In certain embodiments, electrically conductive stitching may be applied to an absorptive pad prior to joining of such a pad to a carrier (e.g., with an intermediate adhesive). In certain embodiments, electrically conductive stitching may be applied to an absorptive pad and a carrier after joining of the pad and carrier. In such a case, the electrically conductive path extends between the first face and second face of the pad but also continues through the carrier.

In embodiments including electrically conductive material that is stitched or woven through one or more layers (e.g., a carrier layer), such conductive material may be stitched or woven in any desirable pattern, preferably including at least some constituents extending in a longitudinal (lengthwise) direction. Examples of patterns for stitching or weaving of conductive material into a carrier include straight longitudinal pattern, zig-zag (e.g., herringbone) pattern, and repeat crossing (e.g., repeating "X") patterns. While each of the foregoing patterns preferably provides at least one substantially continuous conductive path extending in a substantially longitudinal direction, in various embodiments such patterns may be perceived as substantially continuous or non-continuous along one or both faces of a carrier.

According to various embodiments, carrier materials may be formed of suitable materials such as fabrics (e.g., of natural fibers such as cotton, synthetic fibers such as polyester, or non-woven fabrics such as spunbonded polyolefins), polymeric sheets, paper, foil, and the like. Carriers according to various embodiments may consist of a single layer or may include multiple layers of the same or different materials. In certain embodiments, carriers may be coated on one or more faces with conductive materials, moisture barrier materials, and/or other materials providing desired functionality.

In certain embodiments, a carrier defines one or more (preferably multiple) windows enabling access to an electrically conductive material (e.g., electrically conductive layer) arranged along the carrier. Multiple windows may be defined in the inner face, the outer face, or both faces of a carrier. In certain embodiments, a window-defining carrier is intermediately arranged between an electrically conductive (e.g., non-adhesive) material layer and an adhesive layer (with the adhesive layer preferably being electrically conductive). In other embodiments, an electrically conductive (e.g., non-adhesive) material layer may be intermediately arranged between a window-defining carrier and an adhesive layer (with the adhesive layer preferably being electrically conductive). Such an electrically conductive layer may include, for example, a foil, mesh, matrix, coating, or the like.

In certain embodiments, carriers comprising electrically conductive material may be used in conjunction with adhesive pads and/or adhesives comprising electrically conductive materials. Adhesives may be applied in substantially continuous layers or in non-continuous layers (e.g., including discrete portions of adhesive that are separated from or not connected to one another).

In certain embodiments, an adhesive bandage includes an electrically conductive material arranged in or on an absorbent pad to provide an electrically conductive path extending between a first face of the absorbent pad and a second face of the absorbent pad, sufficient to enable actuation of a capacitive touchscreen through the absorbent pad (e.g., optionally overlaid with a carrier) when the absorbent pad is intermediately arranged between skin of a user and the touchscreen.

In certain embodiments, an adhesive bandage includes an electrically conductive material arranged in or on the carrier to provide an electrically conductive path extending between (i) skin of a user not covered by the absorbent pad and (ii) a portion of the carrier covering the absorbent pad, sufficient to enable actuation of a capacitive touchscreen through the carrier when the carrier is intermediately arranged between skin of a user and the touchscreen.

In certain embodiments, an adhesive bandage includes (a) an electrically conductive material is arranged in or on the absorbent pad to provide an electrically conductive path extending between a first face of the absorbent pad to a second face of the absorbent pad, and/or (b) an electrically conductive material is arranged in or on the carrier to provide an electrically conductive path extending between (i) skin of a user not covered by the absorbent pad and (ii) a portion of the carrier covering the absorbent pad. In certain embodiments, the electrically conductive material may include at least one electrical conductor woven into, stitched into (or through), or coated onto, the absorbent pad and/or the carrier. In certain embodiments, the electrically conductive material may comprise an electrically conductive foil or mesh arranged in or in contact with the carrier. In certain embodiments, the adhesive portion of an adhesive bandage or other skin covering element (e.g., athletic tape) is electrically conductive. Such adhesive (preferably a pressure sensitive adhesive) may have an AC impedance over a 2.5 cm×2.5 cm area of preferably no greater than 200 Ohms, preferably no greater than 150 Ohms, preferably no greater than 100 Ohms, preferably no greater than 75 Ohms, preferably no greater than 50 Ohms, preferably no greater than 40 Ohms, preferably no greater than 30 Ohms, or any other suitable value to permit conduction of an electrical signal from a user's skin or fingernail through the adhesive to actuate or control a capacitive touchscreen. Such impedance may be at 10 Hz frequency or any other suitable frequency value.

Certain embodiments relate to use of an adhesive bandage or other skin covering element (e.g., athletic tape) as disclosed herein, the method including applying an adhesive bandage or other skin covering element to at least one of skin and fingernail of a user, and contacting or depressing a portion of the adhesive bandage or other skin covering element against a surface of a capacitive touchscreen of an electronic device to control or operate at least one function of the electronic device.

In certain embodiments, an athletic tape includes a fabric-based carrier including an inner face, an outer face, and an electrically conductive material extending between the inner face and the outer face; and an electrically conductive pressure-sensitive adhesive arranged along the inner face of the carrier. The fabric-based carrier may comprise cotton or any other suitable material. In certain embodiments, at least one electrically conductive material is woven into, stitched into (or through), or coated onto the fabric-based carrier. In certain embodiments, the electrically conductive material comprises an electrically conductive foil or mesh arranged in or in contact with the carrier. In certain embodiments, the electrically conductive material may include metal and/or an electrically conductive polymer.

In certain embodiments, a skin covering element comprises: a carrier including an inner face, an outer face, and a first and a second electrically conductive region extending lengthwise along the carrier; a pressure-sensitive adhesive arranged along the inner face of the carrier; and a first electrical interface in conductive electrical communication with the first and the second electrically conductive region, wherein the first electrical interface is arranged to permit electrical communication with an electrical device. In certain embodiments, the first conductive region and the second conductive region are separated by at least one electrically insulating material (e.g., adhesive, carrier, or other material) associated with the skin covering element.

In certain embodiments, a skin covering element (e.g., including but not limited to athletic tape comprising fabric) includes a second electrical interface arranged to receive a jumper element comprising an electrically conductive material, and to permit conductive electrical communication between the first and the second electrically conductive region when the jumper element is received by the second electrical interface. In certain embodiments, a skin covering element includes a second electrical interface arranged to receive at least one sensor element (e.g., one or more sensor elements such as, but not limited to, sensors adapted to sense pressure, temperature, moisture, humidity, chemical species, acceleration, and the like), wherein the at least one sensor element is in conductive electrical communication with the first and the second electrically conductive region when the at least one sensor element is received by the second electrical interface. In certain embodiments, a skin covering element includes a first or a second electrical interface arranged to receive at least one of a data storage element and a communication element (with the data storage element and/or communication element optionally arranged in electrical communication with at sensor element), wherein the at least one of a data storage element (e.g., a radio frequency identification tag, a flash memory chip, or other memory containing device) and a communication element (e.g., including a wired and/or wireless signal transmitter, receiver, or transceiver) in conductive electrical communication with the first and the second electrically conductive region. A jumper element, at least one sensor element, data storage element, and/or communication element may be removably or non-removably joined or otherwise affixed to the second electrical interface via any suitable method, including adhesives, retaining clips, and/or other mechanical attachment method. In certain embodiments, a jumper element, at least one sensor element, a data storage element, and/or a communication element may be positioned in direct contact with a user's skin; in other embodiments, such element(s) may be arranged with at least one carrier layer positioned between a user's skin and the element(s). In certain embodiments, one or more of jumper element, at least one sensor element, a data storage element, and/or a communication element may be self-powered (e.g., with an associated battery, kinetic energy storage element, or other electrical current generating apparatus) or arranged to receive electric power from an external source through conductive and/or inductive means. In certain embodiments, signals from one or more sensors may be stored using a data storage element, and/or may be communicated using a communication element. Such signals may be further processed for comparison with one another (e.g., to generate trends and/or identify abnormalities) using at least one data processing element. Such signals may include parameters such as pressure, temperature, moisture, humidity, chemical species, acceleration, and the like, as may be useful for monitoring athletic performance, for monitoring or tracking physical therapy, and/or for medical care. Signals from one or more sensors may be indicative of (and therefore be used to track over time) repetitions of motion, range of motion, wrapping/bandaging pressure (as indicative of proper or improper application of a bandage or wrapping), swelling, wetness/dryness, and other phenomena that may be relevant to determining status, improvement, or deterioration of user condition.

In certain embodiments, a first electrical interface and/or a second electrical interface associated with a skin covering element comprises at least one window defined in an inner face or an outer face of a carrier and arranged to expose portions of at least two electrically conductive regions associated with the skin covering element. In certain embodiments, a first electrical interface and/or a second electrical interface associated with a skin covering element may include one or more wires, contacts, and/or other electrical connectors or elements arranged to transmit electrical signals via conductive or inductive communication.

In certain embodiments, wherein the first conductive region comprises a first electrical conductor arranged between the carrier and the adhesive, and the second conductive region comprises a second electrical conductor arranged between the carrier and the adhesive. In certain embodiments, the first and second conductive regions comprise metal foil, electrically conductive mesh, and/or electrically conductive polymer. In certain embodiments, skin covering element including multiple conductive regions further includes an electrically insulating adhesive contacting the conductive regions; in other embodiments, an electrically conductive adhesive is provided with an electrically insulating material intermediately arranged between the adhesive and the electrically conductive regions.

Certain embodiments relate to a method comprising applying a skin covering element as disclosed herein (e.g., athletic tape or other skin covering including multiple electrically conductive regions) to skin of a user, connecting an electrical device to the skin covering element via the first electrical interface and transmitting or receiving at least one electrical signal using the electrical device, the first electrically conductive region, and the second electrically conductive region.

In certain embodiments, an electrical device connected to a skin covering element includes an electric power source (e.g., battery) arranged to apply an electrical signal to the electrically conductive regions for resistive heating thereof, such as may be useful for heating tissue (e.g., skin) of a user covered with the skin covering material, with such signal optionally being controlled responsive to a temperature sensor and/or in conjunction with an adjustable current control element. In certain embodiments, an electrical device connected to a skin covering element includes a signal generator and/or receiver arranged to communicate with at least one sensor (e.g., removably adhered sensor(s)) associated with the skin covering element. In certain embodiments, an electrical device connected to a skin covering element includes a data storage element and/or a communication element.

Certain advantages of providing one or more skin covering elements with multiple electrically conductive regions and electrical interfaces that are distinct from (i.e., not integrated with) other components (e.g., jumpers, sensors, data storage elements, and communication elements) include: (i) the ability to permit a user to regulate the length and/or configuration of skin covering element to cooperate with the other components; (ii) the ability to permit the other components to be selectably affixed to or removed from a skin covering element, for re-use of the other components in order to reduce aggregate cost and waste disposal requirements; (iii) the ability to permit the other components to interface with a variety of different skin covering elements of varying functional characteristics (e.g., size, shape, porosity, materials of construction, etc.) and/or aesthetic characteristics (e.g., color, pattern, and the like).

In certain embodiments, one or more skin covering elements including multiple electrically conductive regions and including one or more electrical interfaces as disclosed herein may be arranged in a kit with at least one of the following elements arranged to cooperate with the one or more skin covering elements via the one or more electrical interfaces: a jumper element, at least one sensor (optionally including sensors of multiple types integrated into a sensor module), a data storage element, and a communication element; and such kit may be contained in a package with operating or usage instructions.

In certain embodiments, one or more skin covering elements as disclosed herein may be arranged in the form of rolls, pre-cut sheets, or strips. Such skin covering elements may be sterilized prior to or after packaging thereof.

Various embodiments are described below with reference to the figures.

Figure 2A:
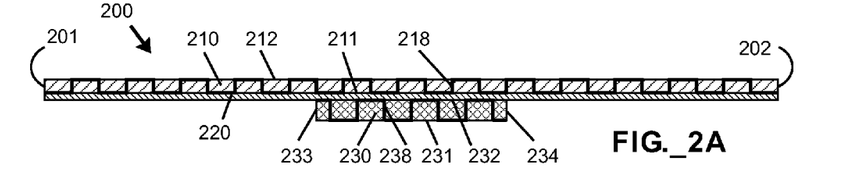
FIG. 2A is a side cross-sectional schematic view of an adhesive bandage according to one embodiment, including an electrically conductive material associated with a carrier, and including an electrically conductive material associated with an absorbent pad.
Figure 2B:
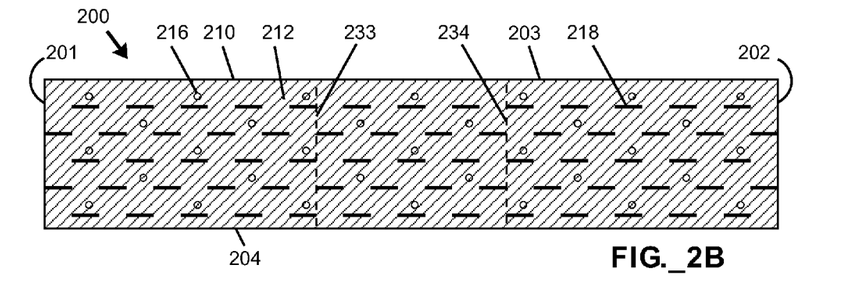
FIG. 2B is a top plan schematic view of the adhesive bandage of FIG. 2A.

FIGS. 2A-2B illustrate an adhesive bandage 200 according to one embodiment, the bandage 200 including a first electrically conductive material 218 associated with a carrier 210, and including a second electrically conductive material 238 associated with an absorbent pad 230. The first and second electrically conductive materials 218, 238 may be of the same or different composition. An adhesive layer 220 (preferably comprising an electrically conductive material) is provided between the carrier 210 and the pad 230, preferably along the length of the bandage 200 between ends 201, 202 thereof. The first electrically conductive material 218 preferably provides a conductive path between opposing faces 211, 212 of the carrier 210, as well as a laterally conductive path (e.g., in a direction perpendicular to bandage ends 201, 202) through or along the carrier 210. Similarly, the second conductive material 238 preferably provides a conductive path between opposing faces 231, 232 of the pad 230, as well as a laterally conductive path (e.g., in a direction perpendicular to pad 233, 234) through or along the pad 230. In certain embodiments, the first and second conductive materials 218, 238 may be prefabricated into the respective carrier layer 210 and/or pad 230 by weaving or stitching prior to mounting of the pad 230 to the carrier 210 (via intermediate adhesive 220), or one or more conductive materials 218, 238 may be applied after mounting of the pad 230 to the carrier (and in such instance, one or more conductive materials may extend through the pad 230, adhesive 220, and carrier 210). As shown in FIG. 2B, the first conductive material 218 may include segments arranged lengthwise along the bandage 200 (e.g., parallel or substantially parallel to a direction extending from the first end 201 to the second end 202). Optional pores or holes 216 may be defined in at least the carrier layer 210 for ventilation.

In operation, the bandage 200 may be applied to skin of a user (e.g., including, but not limited to, along a user's fingertip). The electrically conductive material 238 associated with the pad 230 provides an electrically conductive path from the inner surface 231 to the outer surface 232 of the pad 230 as well as lateral conduction within the pad 230. The adhesive layer 220, which preferably comprises an electrically conductive material, facilitates lateral or axial (e.g., perpendicular to outer face 212) signal conduction. The electrically conductive layer 218 associated with the carrier 210 provides an electrically conductive path from the inner surface 211 to the outer surface 212 of the carrier 210 as well as lateral electrical conduction within the carrier 210. In this manner, a signal can be conducted from a user's skin through any contacting portion of the bandage (e.g., adhesive 220 or pad 230) and through the carrier 210 to an outer surface 211, to permit the user to actuate or control a capacitive touchscreen when the bandage 200 is intermediately placed between the user's skin and the touchscreen.

In certain embodiments, one or more conductive materials may be provided in or on a carrier, absorbent pad, and/or adhesive material of an adhesive bandage in any suitable pattern(s). Various patterns of conductive materials applied to (at least) carrier portions of adhesive bandages are shown in FIGS. 3-5.

Figure 3:
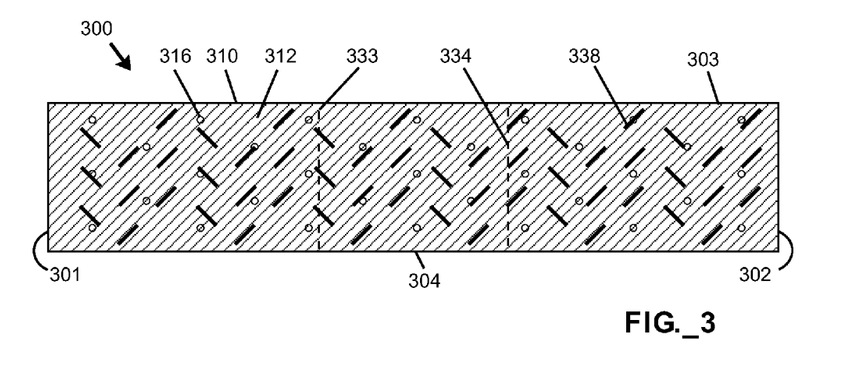
FIG. 3 is a top plan schematic view of an adhesive bandage including an electrically conductive material associated with a carrier according to another embodiment.

FIG. 3 is a top plan schematic view of an adhesive bandage 300 according to one embodiment including a carrier layer 310 with opposing ends 301, 302, lengthwise side edges 303, 304, optional ventilation pores or holes 316, and at least one electrically conductive material 338 arranged in the carrier 310, on the carrier 310, or along the carrier 310 in a non-continuous zig-zag pattern. Portions of the electrically conductive material 338 preferably extends through an entire thickness of the carrier 310, and preferably form one or more substantially continuous electrically conductive paths extending generally lengthwise in, on, or along the bandage 300. An adhesive pad (not shown) having ends 333, 334 is preferably provided along an inner surface of the carrier 310, and preferably joined to the carrier 310 with an adhesive layer (not shown).

Figure 4:
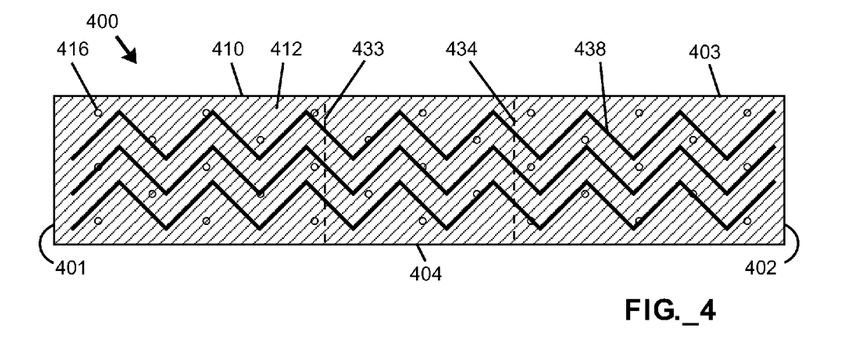
FIG. 4 is a top plan schematic view of an adhesive bandage including an electrically conductive material associated with a carrier according to another embodiment.
Figure 5:
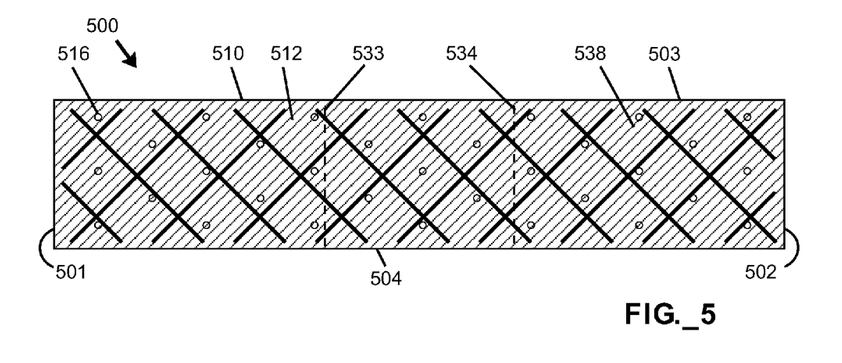
FIG. 5 is a top plan schematic view of an adhesive bandage including an electrically conductive material associated with a carrier according to another embodiment.

FIG. 4 is a top plan schematic view of an adhesive bandage 400 according to one embodiment including a carrier layer 410 with opposing ends 401, 402, lengthwise side edges 403, 404, optional ventilation pores or holes 416, and at least one electrically conductive material 438 arranged in the carrier 410, on the carrier 410, or along the carrier 410 in substantially continuous zig-zag line patterns.

At least portions of the electrically conductive material 438 preferably extends through an entire thickness of the carrier 410, and preferably form one or more substantially continuous electrically conductive paths extending generally lengthwise in, on, or along the bandage 400. An adhesive pad (not shown) having ends 433, 434 is preferably provided along an inner surface of the carrier 410, and preferably joined to the carrier 410 with an adhesive layer (not shown).

FIG. 5 is a top plan schematic view of an adhesive bandage 500 according to one embodiment including a carrier layer 510 with opposing ends 501, 502, lengthwise side edges 503, 504, optional ventilation pores or holes 516, and at least one electrically conductive material 538 arranged in the carrier 510, on the carrier 510, or along the carrier 510 in a pattern of crossing lines or a connected "X" pattern. Portions of the electrically conductive material 538 preferably extends through an entire thickness of the carrier 510, and preferably form one or more substantially continuous electrically conductive paths extending generally lengthwise in, on, or along the bandage 500. An adhesive pad (not shown) having ends 533, 534 is preferably provided along an inner surface of the carrier 510, and preferably joined to the carrier 510 with an adhesive layer (not shown).

One benefit of providing electrically conductive materials in zig-zag or crossing line patterns is that overlapping portions of an adhesive bandage may be more likely to make electrical contact with one another, thereby increasing the likelihood of promoting lateral electrical conduction through portions of a bandage (as may be useful to facilitate control or actuation of a capacitive touchscreen with a finger or appendage covered in part with a bandage).

Figure 6A:
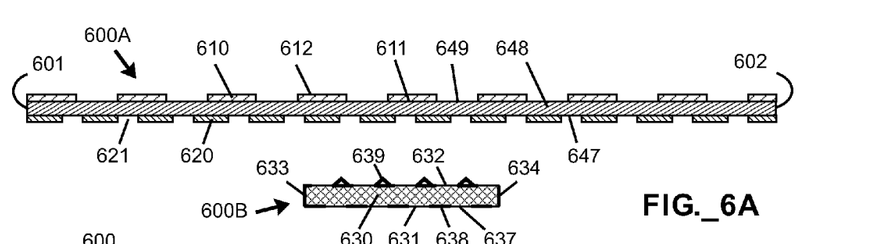
FIG. 6A is a side cross-sectional schematic assembly view of first and second portions of an adhesive bandage according to another embodiment including a carrier with an electrically conductive core.
Figure 6B:
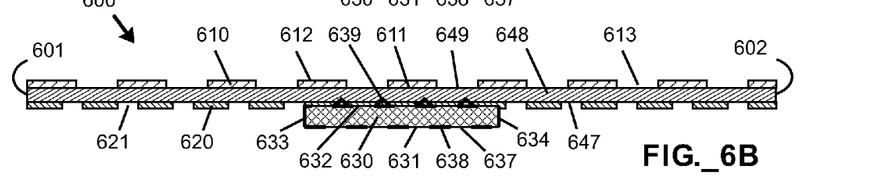
FIG. 6B is a side cross-sectional schematic view of an adhesive bandage including the first and second portions illustrated in FIG. 6A.
Figure 6C:
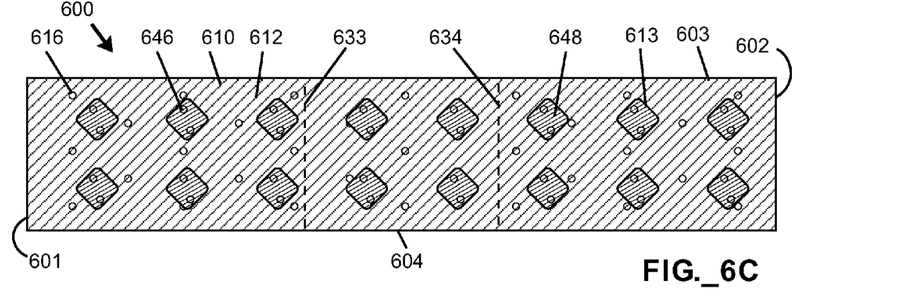
FIG. 6C is a top plan schematic view of the adhesive bandage of FIG. 6B.
Figure 6D:
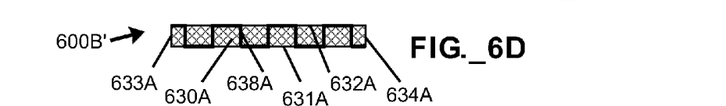
FIG. 6D is a side cross-sectional schematic view of an alternative absorptive pad portion that may be used with the adhesive bandage of FIGS. 6B-6C in an alternative embodiment.

FIG. 6A is a side cross-sectional schematic assembly (partially exploded) view of first and second portions 600A, 600B (including carrier/adhesive portion 600A and pad portion 600B) of an adhesive bandage 600 according to one embodiment including a carrier 610 with an electrically conductive core 648. The assembled bandage 600 is shown in FIGS. 6B-6C. The adhesive bandage 600 includes opposing ends 601, 602, lengthwise side edges 603, 604, optional ventilation pores or holes 616, a carrier 610 defining windows 613, an electrically conductive core 648 (including core faces 647, 649), and an adhesive layer 620 (preferably including an electrically conductive adhesive material) that is optionally non-continuous and/or may define windows 621 (or alternatively may be substantially continuous). An absorbent pad 630 includes an inner face 631, an outer face 632, opposing ends 633, 634, and having an electrically conductive material 638 associated with the pad 630. As illustrated in FIGS. 6A-6B, the electrically conductive material 638 may be provided as a coating or wrapping over the faces 631, 632 of the pad 630 preferably including permeable surface portions 637 along the inner face 631 to permit absorption of exudate from a wound (or alternatively, an electrically conductive material may include portions extending through the pad 630, as shown in FIG. 6D). With continued reference to FIGS. 6A-6B, the electrically conductive material 638 around or along the pad may include one or more electrically conductive protrusions 639 along an outer surface 632 of the pad 630 arranged to promote electrical contact with at least an inner surface 647 of the conductive core 648. One or more portions of the carrier 630 and/or the conductive core 648 may optionally include pores or holes for ventilation.

In operation, the bandage 600 may be applied to skin of a user (e.g., including, but not limited to, along a user's fingertip). The electrically conductive material 638 associated with the pad 630 provides an electrically conductive path from the inner surface 631 to the outer surface 632 of the pad 630 (as well as lateral conduction along the pad 630). The adhesive layer 620, which preferably comprises an electrically conductive material, facilitates lateral or axial (e.g., perpendicular to outer face 612) signal conduction. The electrically conductive core 648 associated with the carrier 610 provides an electrically conductive path between the electrically conductive material 638 associated with the pad 630 to an outer face 649 of the core 648, as well as lateral electrical conduction within the core 648. If the adhesive 620 is electrically conductive, such adhesive may provide axial electrical conduction, and if the adhesive 620 includes at least some continuous portions, the adhesive 620 may also provide lateral electrical conduction. Even if the adhesive is not electrically conductive, (optional) windows or gaps 621 defined in the adhesive layer 620 may enable a user's skin to contact the inner face 647 of the electrically conductive core 648. Similarly, windows or gaps 613 defined in the carrier 610 provide exposed outer face portions 649 of the conductive core 648. In this manner, a signal can be conducted from a user's skin through one or more contacting portions of the bandage (e.g., pad 630, adhesive 620, or conductive core 648) to exposed portions (corresponding to windows 613) of the conductive core 648 along the outer core surface 649, to permit the user to actuate or control a capacitive touchscreen when the bandage 200 is intermediately placed between the user's skin and the touchscreen.

As indicated previously, FIG. 6D illustrates an alternative pad assembly 600B' that could be substituted for the corresponding pad assembly 600B illustrated in FIG. 6A in an adhesive bandage. The pad assembly 600B' includes an absorbent pad 630 with an inner face 631A, an outer face 632A, opposing ends 633A-634A, and an electrically conductive material 638A extending through the pad 630 to provide an electrically conductive path between the inner face 631A and the outer face 632A.

Certain embodiments are directed to skin covering elements other than adhesive bandages. Exemplary embodiments include, but are not limited to, athletic tapes, therapeutic tapes, sensor tapes, and the like.

Figure 7:
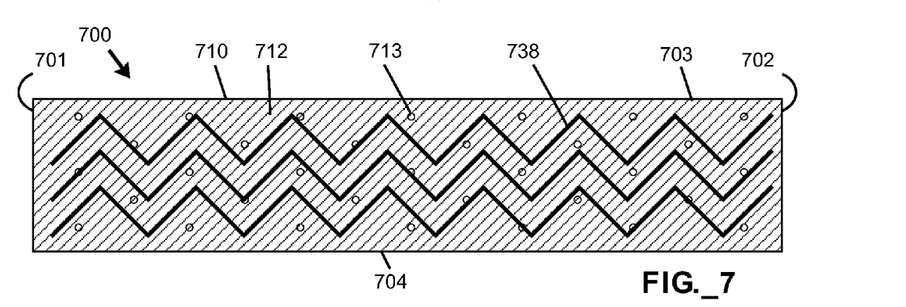
FIG. 7 is a top plan schematic view of a skin covering element (e.g., athletic tape) including at least one electrically conductive material associated with a carrier.

FIG. 7 is a top plan schematic view of a skin covering element (e.g., athletic tape) 700 including at least one electrically conductive material 738 associated with a carrier 710, with the carrier 710 preferably being arranged in contact (along a lower surface thereof) with an adhesive layer (not shown). The skin covering element 700 includes a first end 701, a second end 702, opposing sides 703, 704, and an electrically conductive material 738 arranged in, or, or along (but preferably extending through) the carrier 710. Optional pores or holes 713 may be provided through the carrier for ventilation. FIG. 7 illustrates the electrically conductive material 738 as being arranged as substantially continuous lines in zig-zag patterns. The electrically conductive material 738 may be provided in any suitable other pattern in, on, or along the carrier 710.

Figure 8A:
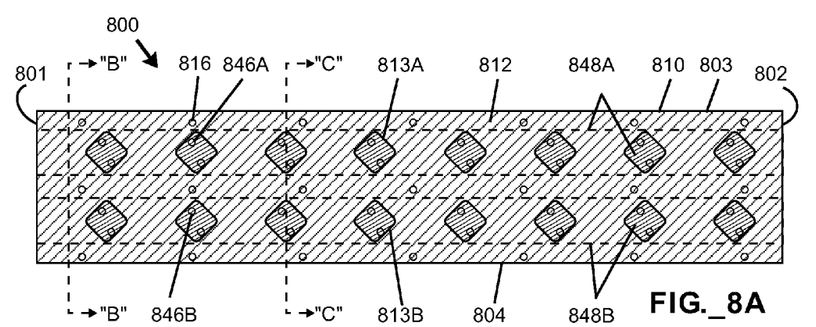
FIG. 8A is a top plan schematic view of a skin covering material (e.g., athletic tape) including first and second longitudinal (lengthwise) conductive regions.
Figure 8B:
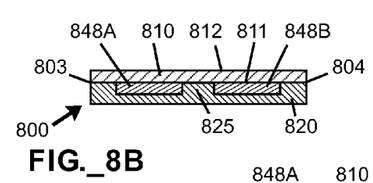
FIG. 8B is a transverse cross-sectional schematic view of the skin covering material of FIG. 8A taken along section lines "B"-"B".
Figure 8C:
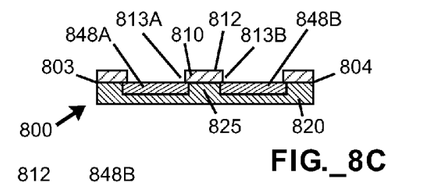
FIG. 8C is a transverse cross-sectional schematic view of the skin covering material of FIG. 8A taken along section lines "C"-"C".

FIGS. 8A-8C illustrate a skin covering material 800 (e.g., athletic tape) including first and second longitudinal (lengthwise) conductive regions 848A, 849B. Although FIGS. 8A-8C illustrate the conductive regions 848A, 849B as being arranged generally between a carrier 810 and an adhesive layer 820, it is to be appreciated that the conductive regions 848A, 849B may be arranged along an (exposed) upper surface 812 of the carrier 810 in alternative embodiments. As shown in FIGS. 8A-8C, the skin covering element 800 includes a first end 801, a second end 802, opposing sides 803, 804, and separate electrically conductive regions 848A-848B arranged between the carrier 810 and an adhesive layer 820. The carrier 810 includes an inner surface 811, an outer surface 812, and windows 813A, 813B defined therein to provide access to the electrically conductive regions 848A-848B, respectively. Optional pores or holes 816, 846A, 846B may be defined in one or more of the carrier 810 and the conductive regions 846A, 846B. The electrically conductive regions 848A-848B are preferably separated from one another, such as by an intermediate portion 825 of the adhesive layer 820 (which may not be electrically insulating in preferred embodiments) and/or by another intervening insulating element (not shown).

Figure 8D:
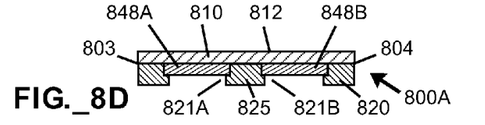
FIG. 8D is a transverse cross-sectional schematic view of an alternative skin covering material similar to that shown in FIG. 8A (e.g., along section lines "B"-"B") but with windows or gaps provided in the adhesive layer.

In alternative embodiments, windows or gaps may be defined in an adhesive layer, such as to enable an electrically conductive path to be established between a user's skin and electrically conductive regions associated with a skin covering element. With reference to FIG. 8D, a skin covering element 800A according to certain embodiments includes a carrier 810, an adhesive layer 820 defining windows 821A-821B, and electrically conductive regions 821A, 821B arranged between the carrier 810 and the adhesive 820, with an intermediate portion 825 of the adhesive serving to separate the electrically conductive regions 821A, 821B.

Figure 9:
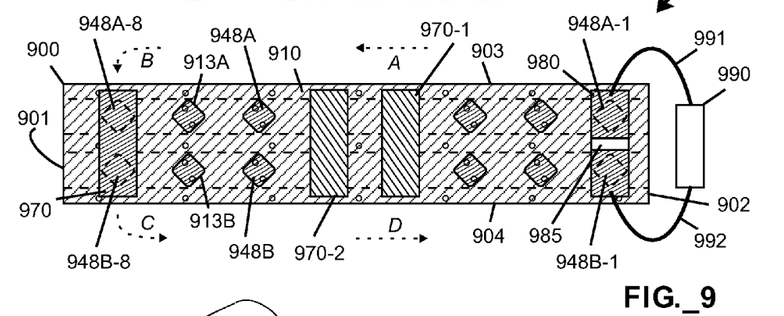
FIG. 9 is a top plan schematic view of a skin covering element according to FIGS. 8A-8C connected to an electrical device along one end and including a jumper element or at least one sensor element along an opposing end.

FIG. 9 illustrates a schematic view of an electrically conductive skin covering system 901 including a skin covering element 900 (substantially similar to the skin covering element described in connection with FIGS. 8A-8C) connected to an electrical device 990 along one end 902 and including a jumper element 970 and/or at least one sensor element 970 along an opposing end 901. The skin covering element 900 includes a carrier 910 arranged over multiple electrically conductive regions 948A, 948B extending in a generally lengthwise direction between side edges 903, 904 thereof. The skin covering element 900 includes various windows 913A, 913B defined in the carrier 910 that expose portions 948A-1 to 948A-8, 948B-1 to 948B-8 of the electrically conductive regions 948A, 948B. Optional insulating elements 970-1, 970-2 may be arranged over various windows 913A, 913B to prevent exposure of certain portions of the electrically conductive regions, with such insulating elements 970-1, 970-2 preferably being subject to removal (e.g., peeling removal) by a user if desired to expose conductive regions.

The jumper element 970 and/or at least one sensor element 970 may be affixed (e.g., by a user, via pressure sensitive adhesive or other attachment means) over exposed portions 948A-8, 948B-8 of the electrically conductive regions 948A, 948B to promote electrical communication between the electrically conductive regions 948A, 948B. In this regard, at least a portion of the jumper 970 preferably comprises an electrically conductive material such as a foil, with such conductive material preferably being overlaid with an insulating material. The electrical device 900 may communicate with the skin covering element 900 via conductors (e.g., wires, cable(s), or the like) 991, 992 and a patch 980 including conductive patch portions arranged to mate with exposed portions 948A-1, 948B-1 of the electrically conductive regions 948A, 948B, with the conductive patch portions separated by an insulator or gap 985.

In operation of the system 901, the jumper 970 and/or at least one sensor 970 is arranged to contact exposed regions 948A-8, 948B-8 constituting one electrical interface to the skin covering element 900, and the patch 980 is arranged to contact exposed regions 948A-1, 948B-1 constituting another electrical interface to the skin covering element 900. An electrical signal may be conducted from the electrical device 990 and conductor 991 through the patch 980 to one electrically conductive portion 948A, through the jumper 970 and/or at least one sensor element 970 to the other electrically conductive portion 948B, and through the patch 980 and conductor 992 back to the electrical device 990. A flow of current through the system 901 is shown with broken line arrows labeled as A, B, C, D. An electrical device and/or sensor(s) of any suitable type as disclosed herein may be used.

Figure 10:
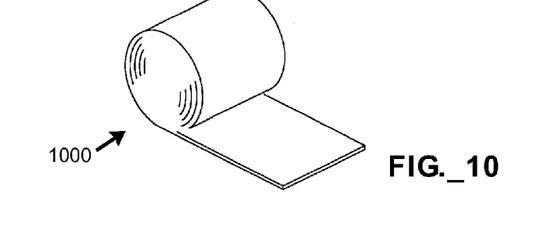
FIG. 10 is a perspective view of a rolled skin covering element.

FIG. 10 is a perspective view of a rolled skin covering element 1000, which may optionally constitute athletic tape. Such skin covering element may be similar in character to the skin covering element disclosed in FIGS. 8A-8C or any other suitable skin covering element as disclosed herein.

Embodiments as disclosed herein may provide one or more of the following beneficial technical effects: enhanced ability of a user to actuate a capacitive touchscreen when a skin covering element (e.g., adhesive bandage or athletic tape) is arranged between the user's skin or fingernail and a touchscreen (without unduly interfering with absorption by of exudate from a wound using a centrally arranged absorbent pad in embodiments directed to bandages); enhanced ability of a skin covering element to alter temperature of a user's joints or tissues covered or wrapped with the skin covering element (e.g., by electrically resistive heating using an external energy source); and enhanced ability of a skin covering element to communicate with at least one electrical device such as at least one sensor, a data storage device, and a communication element.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

The invention claimed is:

1. An adhesive bandage configured to adhere to skin of a user for covering a wound, the adhesive bandage comprising:
   a continuous carrier including an inner face, an outer face, and a pressure-sensitive adhesive arranged along the inner face; and
   an absorbent pad arranged along at least a central portion of the inner face and arranged to contact the wound of the user;
      wherein an electrically conductive material is arranged in or on the absorbent pad to provide an electrically conductive path extending between a first face of the absorbent pad and a second face of the absorbent pad; and
      wherein an electrically conductive material is arranged in or on the continuous carrier to provide an electrically conductive path extending between (i) skin of the user covered by the continuous carrier but not covered by the absorbent pad and (ii) a portion of the continuous carrier covering the absorbent pad.

2. An adhesive bandage according to claim 1, wherein the electrically conductive material arranged in or on the absorbent pad comprises at least one electrical conductor woven into or stitched into the absorbent pad.

3. An adhesive bandage according to claim 1, wherein the electrically conductive material arranged in or on the continuous carrier comprises at least one electrical conductor woven into or stitched into the continuous carrier.

4. An adhesive bandage according to claim 1, wherein the electrically conductive material arranged in or on the continuous carrier comprises an electrically conductive foil or mesh arranged in or in contact with the continuous carrier.

5. An adhesive bandage according to claim 1, wherein the electrically conductive material arranged in or on the absorbent pad and/or the electrically conductive material arranged in or on the continuous carrier comprises an electrically conductive polymer.

6. An adhesive bandage according to claim 1, wherein the pressure-sensitive adhesive is electrically conductive and has an AC impedance of no greater than 200 Ohms over a 2.5 cm×2.5 cm area.

7. An adhesive bandage according to claim 1, wherein the electrically conductive material arranged in or on the absorbent pad comprises at least one electrical conductor coated onto the absorbent pad.

8. An adhesive bandage according to claim 1, wherein the electrically conductive material arranged in or on the continuous carrier comprises at least one electrical conductor coated onto the continuous carrier.

9. An adhesive bandage according to claim 1, wherein the pressure-sensitive adhesive comprises at least one dissolved or dispersed electrically conductive material.

10. An adhesive bandage according to claim 1, wherein the pressure-sensitive adhesive comprises a discontinuous adhesive layer, including discrete portions of adhesive that are not connected to one another.

11. An adhesive bandage according to claim 1, wherein the continuous carrier comprises an electrically conductive layer and a window-defining layer, wherein the window-defining layer defines a plurality of windows enabling access to the window-defining layer.

12. An adhesive bandage according to claim 1, wherein the continuous carrier comprises an electrically conductive matrix.

13. An adhesive bandage according to claim 1, wherein the continuous carrier comprises fabric.

14. An adhesive bandage according to claim 1, wherein the pressure-sensitive adhesive is electrically conductive and has an AC impedance of no greater than 100 Ohms over a 2.5 cm×2.5 cm area.

15. An adhesive bandage according to claim 1, wherein the pressure-sensitive adhesive is electrically conductive and has an AC impedance of no greater than 50 Ohms over a 2.5 cm×2.5 cm area.

16. An adhesive bandage according to claim 1, wherein the pressure-sensitive adhesive is electrically conductive and has an AC impedance of no greater than 30 Ohms over a 2.5 cm×2.5 cm area.

17. An adhesive bandage according to claim 1, wherein the continuous carrier comprises a first plurality of pores or holes, the electrically conductive material arranged in or on the continuous carrier comprises a second plurality of pores or holes, and pores or holes of the first plurality of pores or holes are aligned with pores or holes of the second plurality of pores or holes.

18. An adhesive bandage according to claim 1, further comprising an electrical interface configured for coupling to an electric power source to permit resistive heating.

19. An adhesive bandage according to claim 1, further comprising an electrical interface configured to provide electrical communication with one or more sensors.

20. A method for utilizing an adhesive bandage configured to adhere to skin of a user for covering a wound, the adhesive bandage comprising (A) a continuous carrier including an inner face, an outer face, and a pressure-sensitive adhesive arranged along the inner face, and (B) an absorbent pad arranged along at least a central portion of the inner face and arranged to contact the wound of the user, wherein an electrically conductive material is arranged in or on the absorbent pad to provide an electrically conductive path extending between a first face of the absorbent pad and a second face of the absorbent pad, and an electrically conductive material is arranged in or on the continuous carrier to provide an electrically conductive path extending between (i) skin of the user covered by the continuous carrier but not covered by the absorbent pad and (ii) a portion of the continuous carrier covering the absorbent pad; the method comprising:

applying the adhesive bandage to at least one of skin or a fingernail of a user, thereby placing the skin or fingernail in conductive electrical communication with the electrically conductive path extending between the first face of the absorbent pad and the second face of the absorbent pad, and placing the skin or fingernail in conductive electrical communication with the electrically conductive path extending between (i) the skin of the user covered by the continuous carrier but not covered by the absorbent pad and (ii) the portion of the continuous carrier covering the absorbent pad; and depressing a portion of the adhesive bandage against a surface of a capacitive touchscreen of an electronic device to control or operate at least one function of the electronic device.

* * * * *